United States Patent [19]

Nashef

[11] Patent Number: 4,481,009

[45] Date of Patent: Nov. 6, 1984

[54] POLYMER INCORPORATION INTO IMPLANTABLE BIOLOGICAL TISSUE TO INHIBIT CALCIFICATION

[75] Inventor: Aws S. Nashef, Costa Mesa, Calif.

[73] Assignee: American Hospital Supply Corporation, Evanston, Ill.

[21] Appl. No.: 377,747

[22] Filed: May 13, 1982

[51] Int. Cl.³ .................. A61L 17/00; A63B 51/02; D01C 3/00; D01F 5/00

[52] U.S. Cl. .................................. 8/94.11; 8/94.21; 3/1.5

[58] Field of Search .................. 8/94.11, 94.21, 594, 8/586; 3/1.5

[56] References Cited

U.S. PATENT DOCUMENTS

| | | | |
|---|---|---|---|
| 3,559,652 | 2/1971 | Banitt et al. | 526/298 |
| 3,966,401 | 6/1976 | Hancock et al. | 8/94.11 |
| 4,120,649 | 10/1978 | Schechter | 8/94.11 |
| 4,247,292 | 1/1981 | Angell | 8/94.11 |
| 4,314,800 | 2/1982 | Monsheimer et al. | 8/94.1 R |
| 4,369,036 | 1/1983 | Saito et al. | 8/115.5 |
| 4,378,224 | 3/1983 | Nimni et al. | 8/94.11 |

OTHER PUBLICATIONS

Lloyd, D. R. and Burns, C. M., J. Polymer Science: Polymer Chemistry Edition, 1979, 17, 3459–3472; 3473–3483.

Taylor, M. M. et al., Jalca, 1977, 72, 294–312.

Brauer, G. M. and Termini, D. J., J. Applied Polymer Science, 1973, 17, 2557–2568.

Primary Examiner—A. Lionel Clingman
Attorney, Agent, or Firm—Donald L. Barbeau

[57] ABSTRACT

A process for the preparation of implantable biological tissue, and in particular bioprosthetic heart valves, which are prone to calcification after implantation. The process includes the incorporation of biocompatible polymers into the tissue in an amount effective in reducing calcification of the implanted tissue.

31 Claims, No Drawings

POLYMER INCORPORATION INTO IMPLANTABLE BIOLOGICAL TISSUE TO INHIBIT CALCIFICATION

BACKGROUND OF THE INVENTION

With the introduction of glutaraldehyde preservation of biological tissue, and in particular porcine bioprosthetic heart valves, it has become possible to: (a) overcome the poor performance of early formaldehyde-preserved implanted tissue valves; (b) discontinue the use of homograft valves; and (c) avoid the undesirable use of anticoagulants required to prevent thromboembolism associated with the use of non-bioprosthetic (mechanical) heart valves, especially in children. Not unlike other similarly important discoveries, however it appears that the glutaraldehyde-preserved bioprosthesis has created its own dilemma.

Although the relatively biologically inert glutarladehyde-preserved valves of Carpentier and others have demonstrated excellent long-term durability in most instances, serious drawbacks such as tissue-fatigue and a propensity toward calcification have plagued its continued use. Moreover, it was initially contemplated that children and adolescents would be among those deriving the greatest benefit from the glutaraldehyde-preserved bioprosthetic heart valves since the anticoagulants required with mechanical prosthesis could be eliminated. Results from an increasing number of recent clinical studies indicate that severe calcification of these tissues with relatively short-term failure is prevalent among children and adolescents. Thus, despite their long-term durability and overall reduced incidence of complications, these glutarladehyde-preserved valves have been deemed by some to be unsuitable for use in children.

Calcification of tissue remains a mystery for the most part; however, it has previously been shown that various factors including calcium metabolism diseases, age, diet, degeneration of tissue components such as collagen, and turbulance are all involved to a certain extent. Recently, the occurrence of a specific calcium-binding amino acid, laid down after implantation of glutaraldehyde-preserved porcine xenografts, has been demonstrated; and it has been postulated to play a role in calcification. While calcification has been accompanied by degradative changes in the glutaraldehyde-treated collagen fibers of the implanted tissue, it remains unclear whether the dystrophic calcification is a cause or the result of tissue degeneration. Nevertheless, there has been a continued effort to elucidate the source of the calcification problem with implanted tissue, with the hope that a remedy would be soon to follow. Heretofore, neither the source or cause of calcification in biological implants has been ascertained.

It has separately been proposed that calcification of implanted biological tissue can be reduced by treatment thereof with anionic surfactants, and by avoiding contact of the tissue with phosphate ions prior to implantation. These procedures appear promising in view of their effectiveness in reducing calcification of bioprosthetic heart valve tissue. In addition to reducing calcification, the treatment must preserve the durability of the tissue after implantation. In particular, the treatment must maintain the proper hemodynamic properties of the valve and not adversely affect the stiffness of the valve leaflets.

In accordance with the present invention, we have developed a process which effectively reduces calcification of implanted biological tissue, and maintains the proper hemodynamic properties of the valve leaflets in bioprosthetic heart valves. This process advantageously reduces the tendency of bioprosthesis toward calcification and overcomes some of the problems associated with the durability of xenograft heart valves.

SUMMARY OF THE INVENTION

In accordance with the present invention, disclosed is an improved process for treating biological tissue prior to implantation which results in a mitigation or reduction of calcification thereof after implantation. The process comprises incorporating biocompatible polymers into biological tissue in an amount effective in reducing calcification of said tissue after implantation. In accordance with one embodiment, the process comprises the covalent immobilization of monomers onto the biological tissue followed by further polymerization thereon.

DETAILED DESCRIPTION OF THE INVENTION

In accordance with the present invention, it is contemplated that various types of implantable biological tissue derived from numerous animal sources and parts of the anatomy can be made resistant to calcification. Thus, the tissue can be derived from, inter alia, bovine, porcine, horse, or rabbit; and can include tendons, ligaments, heart valves, or tissue used to construct heart valves such as dura mater and pericardium. It is further contemplated that tissue used for augmentation such as skin patches, pericardial patches, aortic patches, and tympanic membranes is suitable in the present invention. In accordance with a preferred embodiment of the present invention, porcine heart valves or pericardial tissue which was fixed in glutaraldehyde and treated with biocompatible polymeric material was implanted subcutaneously in rabbits. This treated tissue unexpectedly and beneficially effected a sustained mitigation or reduction of calcification after implantation. This sustained mitigation of calcification provides a method of increasing the durability of implanted tissue, particularly of heart valve bioprostheses.

In accordance with the present invention, various polymeric materials can be incorporated into the biological tissue. Examples of polymeric materials which can be used in accordance with this invention include acrylamide, acrylic acid, acrylic acid esters, methacrylic acid, and methacrylamide. We have found acrylamide to be effective in reducing calcification of implanted biological tissue, and thus acrylamide is a preferred polymeric material in accordance with the present invention.

In accordance with the present invention, the polymeric material can either be impregnated into the biological tissue by inclusion within the interstices of the tissue to form a physical or mechanical bond, or it can be chemically bonded thereto. Covalent bonding has the advantage that the polymeric material will not be displaced from the tissue after implantation nor be subject to dislocation of layers within the tissue, and is thus the preferred technique. A number of functional chemical groups suitable for covalent bonding are present in proteins and include $\alpha$- and $\epsilon$-amino groups; $\alpha$-, $\beta$-, and $\gamma$-carboxyl groups; the sulfhydryl and hydroxy groups of cysteine and serine; the imidazole group of histidine;

and the phenol ring of tyrosine. Techniques for chemically attaching chemical groups to these residues are well known. Furthermore, the mucopolysaccharides of biological tissue have free carboxyl groups on which a variety of monomers can be attached. We have found that covalent bonding of monomers to the biological tissue followed by further polymerization with biocompatible polymers is effective in reducing calcification after implantation, and thus is the preferred process in accordance with the present invention. This is achieved either through direct coupling or through coupling agents as described hereinafter.

It is contemplated that a consequence of incorporating polymers into tissue is that the spaces within the tissue will be filled and thus possibly reduce the penetration of plasma proteins and cellular material of the host into the implanted tissue. This penetration is alleged to contribute to degenerative changes in heart valve tissue resulting in early valve failure. It is further contemplated that covalently bound polymeric material may increase the mechanical strength of the tissue.

In accordance with a preferred embodiment of the present invention, various coupling agents can be used to couple the polymeric material to the tissue. In one embodiment, diamines are used to bond a variety of monomers to the free carboxyl residues on the protein and mucopolysaccharide components of the tissue with the aid of an activating factor, such as carbodiimide. Examples of this type of coupling are illustrated by Lloyd and Burns in *Journal of Polymer Science: Polymer Chemistry Edition*, Vol. 17, pp 3459–3483 (1979). Preferred diamines in accordance with the present invention include those having the formula $R-(NH_2)_2$ wherein R is an aliphatic group having straight, branched, or cyclic chain; or an aromatic group. It is contemplated that the chain length or bulkiness of R should be such that the diamine can freely diffuse within the protein network of the tissue. Preferably the diamine should be water-soluble. The most preferred diamine in accordance with the present invention is ethylenediamine.

In accordance with a preferred embodiment of the present invention, a monomer capable of further polymerization is coupled to the tissue via the diamine spacer described above. In one embodiment acrylic acid or its derivatives is preferred. In a more preferred embodiment of the present invention, only covalently coupled polymer is desired on the tissue. Thus, the tissue is thoroughly rinsed after incorporation of acrylic acid to flush out any non-covalently bonded acrylic acid monomer entrapped within the tissue. This non-bonded monomer would promote homopolymerization when the additional polymer is incorporated in the tissue. Homopolymerization, the formation of polymer which is not covalently immobilized to the tissue, depletes available monomer for covalent coupling; thus altering the desired properties of the treated tissue.

As described above, various polymeric materials are suitable for incorporation into biological tissue in accordance with the present invention. Various physical properties can be achieved by altering the nature of the polymer; such as charge, hydrophobicity, and hydrophilicity. The amount of polymerization and the degree of crosslinking can also be varied to achieve the desired properties. In accordance with a preferred embodiment, the monomer coupled to the tissue is further polymerized in an effective amount by suspension in a solution of from about 0.5 to about 6 weight percent acrylamide or similar monomer. More preferably the solution is from about 0.5 to about 2 weight percent; and most preferably 1 weight percent. The acrylamide is crosslinked using about 0.25 weight percent bisacrylamide.

In accordance with the present invention, it is preferable to store and fix the tissue within a tissue-stabilizing pH range; that is, within a pH range that is not deleterious to the tissue components. A preferred pH range is from about 7.0 to about 7.6, and a more preferred pH range is from about 7.1 to about 7.4. The most preferred pH in accordance with the present invention is 7.3.

Buffers used in accordance with on embodiment of the present invention are preferably stable, non-interacting with the stabilization process, and have a buffering capacity sufficient to maintain an acceptable pH, particularly during the fixation of the tissue. The choice of the appropriate buffer, and its concentration will depend upon specific tissue preparation conditions; variations of which have been introduced by several manufacturers. The buffers can be either conventional 0.01–0.02M phosphate-buffered saline (PBS) or phosphate-deficient solutions such as those containing less phosphate than these 0.01 to 0.02M PBS solutions, and preferably less than about 0.001 to about 0.002M phosphate. Preferred buffers in accordance with the present invention include borate, carbonate, bicarbonate, cacodylate (found to be non-toxic in animals), and other synthetic, artificial, or organic buffers such as HEPES, N-2-hydroxyethylpiperazine-N'-2-ethanesulphonic acid; MOPS, morpholine propanesulphonic acid; and PIPES, 1,4-piperazinediethanesulphonic acid. We have found that tissue prepared in HEPES buffer advantageously results in a significant reduction of calcification after implantation, and is therefore most preferred in the present invention.

Preferably, the buffered or unbuffered solutions, used in accordance with the present invention should not interfere with the tissue stabilizing process afforded by fixing agents such as glutaraldehyde. That is, they should not react with the fixing agent or prevent the fixing agent from achieving proper fixation of the tissue. Illustrative of this are buffers containing primary and secondary amines such as tris(hydroxymethyl)aminomethane (Tris), which are known to react with the aldehyde groups of glutaraldehyde and thus interfere with the normal tissue stabilization process.

In accordance with the present invention, the tissue is fixed (tanned) in 0.625 weight percent glutaraldehyde.

The present invention is further illustrated by the following examples which are not intended to be limiting:

EXAMPLE I

Extracted porcine aortic heart valve tissue was thoroughly rinsed and shipped in an isotonic (285±15 milliosmols) solution containing 0.54 grams/liter of the sodium salt of HEPES and 0.885 weight percent sodium chloride at pH 7.3 at about 4° C.; and fixed with 0.625 weight percent glutaraldehyde in an isotonic solution containing 5.39 grams/liter of the sodium salt of HEPES, 0.440 weight percent sodium chloride, and 2.6 grams/liter of $MgCl_2.6H_2O$ at room temperature.

EXAMPLE II

The extracted tissue of Example I was further sterilized in a solution containing about 4% formaldehyde, rinsed in sterile saline to remove residual glutaraldehyde at a time immediately prior to implantation, and implanted subcutaneously in growing rabbits. The valve tissue was retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections.

EXAMPLE III

About 5 grams (wet) extracted tissue prepared according to the procedure of Example I was immersed in a 40 ml solution containing about 1 gram of ethylenediamine at pH 4.75. After about 30 minutes, 1 gram of water-soluble 1-ethyl-3(3-dimethylaminopropyl) carbodiimide-HCl was added stepwise while the pH was maintained at 4.75 for a 30 minute incubation period at room temperature. The pH is preferably controlled to 4.75±0.1 in order to ensure maximum reactivity of the diamine with the carboxylate group. Next, the tissue was rinsed thoroughly with HEPES-buffered-saline at pH 7.4 and transferred into an aqueous solution containing 0.2M acrylic acid at pH 4.75 for about 30 minutes. The tissue was then thoroughly rinsed with HEPES-buffered-saline to remove any non-coupled acrylic acid from the tissue. The acrylic acid-coupled tissued was then further suspended in about 40 ml distilled water and bubbled with nitrogen for about 30 minutes before replacing with a 40 ml solution of 2 percent ammonium persulfate containing 0.6% (v/v) N,N,N',N'-tetramethylenediamine which was previously bubbled with nitrogen for 30 minutes. After 30 minutes, the free radical initiation step was completed and the tissue was transferred to 40 ml of 0.5 weight percent acrylamide solution containing 0.25% bisacrylamide (N,N'-methylbisacrylamide) for 30 minutes to replace the persulfate solution. All tissue transfer steps were performed in a nitrogen atmosphere. After the reaction mixture was allowed to polymerize for about 60 minutes, the tissue was rinsed with distilled water, sterilized in a solution containing 4% formaldehyde, rinsed again in sterile saline and implanted subcutaneously in growing rabbits. The valve tissue was retrieved up to six weeks later at regular one-week intervals; and the extent of tissue calcification was assessed by quantitatively monitoring the weight percent calcium in dried tissue using atomic absorption analysis, and histologically by visually monitoring the degree of calcification in Von Kossa-stained tissue sections. Both the histologic and quantitative results indicate that the implanted valve tissue having acrylamide incorporated thereon effected a significant reduction in calcification compared to the valve tissue treated according to the process of Example II. Moreover, the valve tissue having acrylamide incorporated thereon did not exhibit any deleterious effects with respect to the stiffness of valve leaflets when the tissue was mounted in a bioprosthetic heart valve and tested by conventional steady and pulsative flow tests.

EXAMPLE IV

The retrieved tissue of Examples II and III was further analyzed to assess the integrity of the tissue after implantation. The results of our analysis indicate that there was no significant difference in: shrinkage temperature; moisture content; or amino group analysis.

EXAMPLE V

Extracted bovine pericardial tissue was thoroughly rinsed and shipped in an isotonic (285±15 milliosmols) solution containing 0.54 grams/liter of the sodium salt of HEPES and 0.885 weight percent sodium chloride at pH 7.3 at about 4° C.; and fixed with 0.625 weight percent glutaraldehyde in an isotonic solution containing 5.39 grams/liter of the sodium salt of HEPES, 0.440 weight percent sodium chloride, and 2.6 grams/liter of $MgCl_2.6H_2O$ at room temperature.

EXAMPLE VI

The extracted tissue of Example V was further sterilized in a solution containing about 4% formaldehyde, rinsed in sterile saline to remove residual glutaraldehyde at a time immediately prior to implantation, and implanted subcutaneously in growing rabbits. The tissue was retrieved up to six weeks later at regular one-week intervals. After retrieval, the extent of tissue calcification was assessed by quantitatively monitoring the weight percent calcium in dried tissue using atomic absorption analysis; and histologically by visually monitoring the degree of calcification in Von Kossa-stained tissue sections.

EXAMPLE VII

About 5 grams (wet) extracted tissue prepared acording to the procedure of Example V was immersed in a 40 ml solution containing about 2.5 grams of ethylenediamine at pH 4.75. After about 30 minutes, 2 grams of water-soluble 1-ethyl-3(3-dimethylaminopropyl) carbodiimide-HCl was added stepwise while the pH is maintained at 4.75 for a 30 minute incubation period at room temperature. The pH is preferably controlled to 4.75±0.1 in order to ensure maximum reactivity of the diamine with the carboxylate group. Next, the tissue was rinsed thoroughly with HEPES-buffered-saline at pH 7.4 and transferred into an aqueous solution containing 0.2M acrylic acid at pH 4.75 for about 30 minutes. The tissue was then thoroughly rinsed with HEPES-buffered-saline to remove any non-coupled acrylic acid from the tissue. The acrylic acid-coupled tissue was then further suspended in about 40 ml distilled water and bubbled with nitrogen for about 30 minutes before replacing with a 40 ml solution of 2 percent ammonium persulfate containing 0.6% (v/v) N,N,N',N'-tetramethylenediamine which was previously bubbled with nitrogen for 30 minutes. After 30 minutes, the free radical initiation step was completed, and the tissue was transferred to 40 ml of a 1 weight percent acrylamide solution containing 0.25% bisacrylamide (N,N'-methylbisacrylamide) for 30 minutes to replace the persulfate solution. All tissue transfer steps were performed in a nitrogen atmosphere. After the reaction mixture was allowed to polymerize for about 60 minutes, the tissue rinsed with distilled water, sterilized in a solution containing 4% formaldehyde, rinsed again in sterile saline and implanted subcutaneously in growing rabbits. The tissue was retrieved up to six weeks later at regular one-week intervals; and the extent of tissue calcification was assessed by quantitatively monitoring the weight percent calcium in dried tissue using atomic absorption analysis, and histologically by visually monitoring the degree of calcification in Von Kossa-stained tissue sections. Both the histologic and quantitative results indicate that the implanted tissue having acrylamide incorporated thereon effected a significant reduction in calcification compared to the tissue treated according to the process of Example VI. Moreover, the tissue having acrylamide incorporated thereon did not exhibit any deleterious effects with respect to the stiffness of valve leaflets when the tissue was mounted in a bioprosthetic heart valve and tested by conventional steady and pulsative flow tests.

The present invention has been described in specific detail and in reference to its preferred embodiments; however, it is to be understood by those skilled in the art that modifications and changes can be made thereto without departing from the spirit and scope thereof.

I claim:

1. A process for treating animal biological tissue prior to implantation in an animal to reduce calcification of said tissue after implantation comprising the steps of:
   (a) fixing said tissue under tissue fixing conditions;
   (b) contacting said fixed tissue with a first solution of a monomer capable of further polymerization for a time sufficient to covalently bind said monomer directly to the tissue; and
   (c) contacting said tissue with a second monomer solution under polymerization conditions such that said second monomer polymerizes with said first monomer bound to said tissue in an amount effective in reducing calcification of said tissue after implantation.

2. The process of claim 1 further comprising the step of removing non-covalently bound monomer from said tissue between steps (b) and (c).

3. The process of claim 1 wherein said first monomer is acrylic acid or methacrylic acid.

4. The process of claim 1 wherein said second monomer solution comprises acrylamide, acrylic acid, acrylic acid ester, methacrylic acid, or methacrylamide.

5. The process of claim 1 wherein said first monomer is acrylic acid or methacrylic acid, and said second monomer solution comprises acrylamide, acrylic acid, acrylic acid ester, methacrylic acid, or methacrylamide.

6. The process of claim 1 wherein the first monomer covalently bound to said tissue is acrylic acid, and the second monomer solution comprises acrylamide and bisacrylamide.

7. The process of claim 2 wherein the first monomer covalently bound to said tissue is acrylic acid, and the second monomer solution comprises acrylamide and bisacrylamide.

8. The process of claim 6 or 7 wherein the second monomer solution contains from about 0.5 to about 6 weight percent acrylamide.

9. The process of claim 8 wherein the second monomer solution further contains about 0.25 weight percent bisacrylamide.

10. The process of claim 1 or 2 wherein said biological tissue is tendon, ligament, heart valve, dura meter, or pericardium.

11. The process of claim 10 wherein said biological tissue is fixed with glutaraldehyde.

12. A process of treating animal biological tissue prior to implantation in an animal to reduce calcification of said tissue after implantation comprising the steps of:
   (a) fixing said tissue under tissue fixing conditions;
   (b) covalently binding a spacer to said fixed tissue;
   (c) contacting said fixed tissue with a first solution of a a monomer capable of further polymerization for a time sufficient to covalently bind said monomer to the spacer; and
   (d) contacting said tissue with a second monomer solution under polymerization conditions such that said second monomer polymerizes with said first monomer bound to said tissue through said spacer in an amount effective in reducing calcification of said tissue after implantation.

13. The process of claim 12 further comprising the step of removing non-covalently bound monomer from said tissue between steps (c) and (d).

14. The process of claim 12 wherein said first monomer is acrylic acid or methacrylic acid.

15. The process of claim 12 wherein said spacer is a diamine compound.

16. The process of claim 12 wherein said tissue is contacted with carbodiimide between steps (c) and (d).

17. The process of claim 12 wherein said second monomer solution comprises acrylamide, acrylic acid, acrylic acid ester, methacrylic acid, or methacrylamide.

18. The process of claim 12 wherein said first monomer is acrylic acid or methacrylic acid, and said second monomer solution comprises acrylamide, acrylic acid, acrylic acid ester, methacrylic acid, or methacrylamide.

19. The process of claim 13 wherein the first monomer covalently bound to said tissue is acrylic acid, and the second monomer solution comprises acrylamide and bisacrylamide.

20. The process of claim 17 wherein the second monomer solution contains from about 0.5 to about 6 weight percent acrylamide.

21. The process of claim 15 wherein said diamine compound has the formula $$R-(NH_2)_2$$

wherein R is an aliphatic group having a straight, branched or cyclic chain, or an aromatic group.

22. The process of claim 20 wherein the second monomer solution further contains about 0.25 weight percent bisacrylamide.

23. The process of claim 12 or 13 wherein said biological tissue is tendon, ligament, heart valve, dura meter, or pericardium.

24. The process of claim 23 wherein said biological tissue is fixed with glutaraldehyde.

25. A process for treating animal biological tissue prior to implantation in an animal to reduce calcification of said tissue after implantation comprising the steps of:
   (a) fixing said tissue under tissue fixing conditions;
   (b) contacting said tissue with a first monomer capable of further polymerization for a time sufficient to impregnate said monomer in said tissue; and
   (c) contacting said tissue with a second monomer solution under polymerization conditions such that said second monomer polymerizes with said first monomer impregnated within said tissue in an amount effective in reducing calcification of said tissue after implantation.

26. The process of claim 25 wherein said first monomer is acrylic acid or methacrylic acid.

27. The process of claim 25 or 26 wherein said second monomer solution comprises acrylamide, acrylic acid, acrylic acid ester, methacrylic acid, or methacrylamide.

28. A method for reducing calcification of fixed animal biological tissue after implantation in an animal comprising: covalently immobilizing a monomer capable of further polymerization onto said biological tissue, and polymerizing a second monomer which may be the same as the first monomer with said first monomer immobilized on said tissue prior to implantation in an amount effective in reducing calcification after implantation.

29. The method of claim 28 wherein said first monomer is acrylic or methacrylic acid which is covalently bound to said tissue; said second monomer is acrylamide, acrylic acid, acrylic acid ester, methacrylic acid, or methacrylamide; and said tissue is fixed with glutaraldehyde.

30. The method of claim 29 wherein the biological tissue is tendon, ligament, heart valve, dura mater, or pericardium.

31. A bioprosthetic heart valve having a reduced tendency toward calcification after implantation in an animal, said heart valve comprising animal biological tissue having crosslinked hydrophilic polymers covalently immobilized thereon according to the process of claim 2 or 13.

* * * * *